United States Patent [19]

Rubin

[11] Patent Number: 4,762,705
[45] Date of Patent: Aug. 9, 1988

[54] CANCER THERAPY WITH INTERFERON

[75] Inventor: David Rubin, 5 Rav Zair, Jerusalem, Israel

[73] Assignees: Adolf W. Schwimmer, Savyon, Israel; Irwin Steven Schwartz, Tel-Aviv, Israel; David Rubin, Jerusalem, Israel

[21] Appl. No.: 594,436

[22] Filed: Mar. 29, 1984

Related U.S. Application Data

[63] Continuation of Ser. No. 320,088, Nov. 10, 1981, abandoned.

[51] Int. Cl.$^4$ ............................................. A61K 45/02
[52] U.S. Cl. ...................................... 424/85; 530/351
[58] Field of Search .......................................... 424/85

[56] References Cited

PUBLICATIONS

Lerner, Article in Methods in Enzymology, vol. II, pp. 827–831 (1955).
Chemical Abstracts, vol. 84, Abstract No. 69303c, 1976.
Chemical Abstracts, vol. 91, Abstract No. 83177r, 1979.
Mazzara-Porro, M., et al., Pigment Cell, vol. 4, pp. 234–243, 1979.
Johnson, R, JAMA, vol. 245, No. 2, pp. 109–116, 1981.
Priestman, T. J., "Interferon: An Anti–Cancer Agent?" Cancer Treatment Reviews, 6, 223–237 (1979).
Sikora, K., "Does Interferon Cure Cancer?" British Medical Journal, 281, pp. 855–858 (1980).
Chen, Y. M. et al, "Serum Tyrosinase in Malignant Disease, Its Activity, and the Electrophoretic Patterns of the Enzyme as Carried by Immunoglobulins", Cancer Research, 39, pp. 3485–3490 (1979).
Sizer, I. W., "Oxidation of Proteins by Tyrosinase and Peroxidase", Advances in Enzymology, 14, 129–159, (1953).
Warren, S. L., "A Practitioner's Guide to Interferon", Annals of Allergy, 45, pp. 37–42, (1980).
Zoon, K. C. et al, "Amino Terminal Sequence of the Major Component of Human Lymphoblastoid Interferon", Science, 207, p. 527 (1980).
Knight, Jr., E. "Human Fibroblast Interferon: Amino Acid Analysis and Amino Terminal Amino Acid Sequence", Science, 207, pp. 525–526 (1980).
Houghton, M., et al, "The Complete Amino Acid Sequence of Human Fibroblast Interferon as Deduced Using Synthetic Oligodeoxyribonucleotide Primers of Reverse Transcriptase", Nucleic Acids Research, vol. 8, No. 13, 2885–93 (1980).
Nazzaro-Porro, M. et al, "Identification of Tyrosinase Inhibitors in Cultures of Pityrosporum", The Journal of Investigative Dermatology, 71:205–208 (1978).
Breathnach, A. S., et al, "Effect of Dicarboxylic Acids on Normal Human Melanocytes in Dispersed Tissue Culture", British Journal of Dermatology, 101, pp. 641–649 (1979).
Nazzaro-Porro M. et al, "Effect of Azelaic Acid on Human Malignant Melanoma", The Lancet, May 24, 1980, pp. 1109–1111.
Dawson, C. R. et al, "Plant Tyrosinase (Polyphenol Oxidase)", Methods in Enzymology, 2, 817–827 (1955).
McCarty, M. F., Non-Toxic Inhibition of Extracellular Tumor Enzymes—Potential In Cancer Therapy, Medical Hypothesis, 8, 303–310, 1982.
Rubin, D. M., et al., "The Possible Role of Tyrosinase in Malignant Growth", Medical Hypothesis, 10:469–471 (1983).

Primary Examiner—Blondel Hazel
Attorney, Agent, or Firm—Browdy and Neimark

[57] ABSTRACT

The effectiveness of interferon for treatment against cancer may be increased by first administering an agent for inhibiting tyrosinase. In this manner the tyrosinase which is known to be produced by malignancies, and which may cause inactivation of the interferon, will be substantially inactivated prior to the interferon administration.

9 Claims, No Drawings

CANCER THERAPY WITH INTERFERON

This application is a continuation of application Ser. No. 320,088 filed Nov. 10, 1981.

FIELD OF THE INVENTION

The present invention relates to an improved method of cancer therapy using interferon and, more particularly, to a method in which the denaturation of the interferon during treatment is substantially eliminated.

BACKGROUND OF THE INVENTION

Since its discovery in 1957, interferon has been extensively studied. Although initially considered as an antiviral substance, evidence has accumulated that interferon also has anti-tumor activity. These are many reports in the literature of clinical studies with interferon in cancer. These are summarized, for example, in Priestman, P. J. "Interferon: an Anti-Cancer Agent?" *Cancer Treatment Reviews* (1979) 6, 223–237. See also Sikora, K. "Does Interferon Cure Cancer?" *British Medical Journal*, Sept. 27, 1980, 281 (6244) 855-8. All of these clinical tests have required enormous amounts of interferon, usually in the range of from 3,000,000 to 10,000,000 units of interferon per day, administered until remission, complication, or lack of adequate therapeutic response dictates a halt in therapy. Notwithstanding such enormous amounts of interferon, the results of these clinical trials have not yet proven particularly effective, other than to cause a slight increase in the average survival time of the cancer patients. The extremely high dose rates used for cancer treatment should be contrasted to the low dose therapy using only thousands of units which has been reported as efficaceous in aborting and treating common "cold" and flu symptoms with interferon.

These high dose rates have known side effects which include myelosuppression, pyrexia, etc. In view of the large dosages required, the known side effects, and the high price of interferon, it appears that, in the manner in which it is used to date, interferon is a failure for the treatment of cancer.

It is the belief of the present inventor that the reason why interferon fails, even while administered in very large amounts, is because of denaturation of the interferon in vivo due to a substance known to be produced in persons with malignant diseases.

It is known from Chen. Y. M. et al "Serum Tyrosinase in Malignant Disease, Its Activity, and the Electrophoretic Patterns of the Enzyme as Carried by Immunoglobulins", *Cancer Research*, 39, 3485–90, September, 1979, that most malignant tumors exhibit an abnormally high tyrosinase activity so that the level of tyrosinase that is transferred to the serum is between 50% and 600% higher than the tyrosinase activity of normal individuals.

It is also known that tyrosinase not only attacks the amino acid tyrosine but also attacks tyrosine when contained in the polypeptide chain of a protein. In fact, it has been shown in the review Sizer, I. W. "Oxidation of Proteins by Tyrosinase and Peroxidase," *Advances in Enzymology*, 14, 129–159 (1953), that many proteins are biologically inactivated by tyrosinase in view of the oxidation of the tyrosyl groups in the protein by the tyrosinase.

Interferon is a protein of low molecular weight whose amino acid composition includes substantial amounts of tyrosine. It has been reported that chick embryo interferon contains 2.3% tyrosine. It has also recently been reported that human fibroblast interferon contains 4.4% tyrosine, and that tyrosine is the third amino acid in the amino-terminal amino acid sequence of the human fibroblast interferon. Furthermore, it has recently been reported that human lymphoblastoid interferon contains 2.3% tyrosine.

That denaturation of interferon is indeed actually caused by tyrosinase has been proved by the present inventor in the following experiment.

Tyrosinase in the amount of 0.01 mM was incubated in vitro with 5000 units of human leucocyte interferon for 30 minutes. In the course of this incubation the color of the interferon turned from substantially transparent to brown. Such a color change is one indication of denaturation. Measurement of oxidation demand during this incubation also demonstrated that oxidation took place.

Accordingly, the present inventor believes that interferon fails to exert its activity on most malignancies because of the denaturating enzymatic process to which it is subjected first in the blood and then at the cancer site, by the tyrosinase of the malignant growth.

SUMMARY OF THE INVENTION

Accordingly, it is an object of the present invention to improve the effects of interferon in cancer therapy.

It is a further object of the present invention to substantially eliminate any denaturating activity on interferon caused by tyrosinase.

These and other objects of the present invention are attained by the treatment of the cancer patient with a tyrosinase inhibitor before and/or during the treatment with interferon. This use of tyrosinase inhibitor will result in a remarkable effect of the interferon against malignancies in much lower dosages.

DETAILED DESCRIPTION OF PREFERRED EMBODIMENTS

Tyrosinase is known to be a copper-protein enzyme which requires copper in order to exhibit any enzymatic activity. Thus, any chemical that can chelate or complex copper ions will be an inhibitor or tyrosinase. The use of such a tyrosinase inhibitor will inhibit or eliminate much of the tyrosinase activity caused by malignant growths and will thus prevent denaturation of interferon.

Compounds known to be non-competitive tyrosinase inhibitors include diethyldithiocarbamate, sodium sulfide, potassium ethyl xanthate, sodium azide, salicylaldoxime, p-aminobenzoic acid, sulfathiazole and other thiazole derivatives, thiouracils, thioureas, cysteine, glutathione, BAL (dimercaprol), thioproline, hydroquinone and its derivatives, and mercaptoamines.

Of those compounds which are known to be tyrosinase inhibitors, the most preferable for use in accordance with the present invention are those with the least amount of toxicity, since these chemicals would be administered internally. D-penicillamine, while not previously disclosed as a tyrosinase inhibitor, is a known copper-complexing agent and thus serves as a tyrosinase inhibitor. Since this compound is substantially non-toxic and has been administered internally previously, it is the preferred compound for administration in accordance with the present invention.

Certain non-toxic competitive inhibitors of tyrosinase can also be used, preferably simultaneously with other non-competitive inhibitors. For example, certain dicarboxylic acids are competitive inhibitors of tyrosinase, and are known to be substantially non-toxic. $C_{8-13}$ dicarboxylic acids are specifically known to be competitive inhibitors of tyrosinase, but it is believed that other, particularly higher molecular weight, dicarboxylic acids will also be suitable for this purpose. Certain catechols are also known as competitive inhibitors of tyrosinase.

Furthermore, it has been disclosed in U.S. patent application Ser. No. 320,087 by the present inventor and another, filed on even date herewith, that certain straight chain saturated aliphatic dicarboxylic acids having a total number of carbon atoms divisible by four are relatively toxic to certain tumor cells while non-toxic to normal cells of the same origin. Such dicarboxylic acids may also be competitive inhibitors of tyrosinase, as discussed hereinabove, so their use is also comprehended by the present invention.

The preferred practical procedure for complexing copper and thus inhibiting tyrosinase, is the same as the known treatment for Wilson's disease, which is a rare hereditary disorder in which there is an abnormal accumulation of copper in the body. Copper has been complexed and excreted from the human body in the treatment of Wilson's disease through use of the compound D-penicillamine.

The simultaneous administration of a non-competitive inhibitor, such as D-penicillamine, and a competitive inhibitor, such as $C_{12}$-dicarboxylic acid, will have synergistic effects and such combined use is preferred.

The amount of tyrosinase in the bloodstream can be monitored during the treatment with tyrosinase inhibitor in order to determine when a substantial amount of tyrosinase has been inactivated. At that time, the interferon treatment may begin. The required dosage will be less than that required without tyrosinase in view of the fact that the denaturation of the interferon being administered will not be a problem. The effective amount of interferon can be empirically determined in order to arrive at the optimum dosage. Similarly, the dosage of tyrosinase inhibitor can be empirically determined based on the assay of the tyrosinase activity in the blood stream. Generally, however, these dosages will be similar to those known for the treatment of Wilson's disease.

The tyrosinase inhibitor and the interferon preparation may be administered sequentially or simultaneously in order to inactivate the tyrosinase before or during administration of the interferon. Simultaneous administration is possible in view of the almost instantaneous action of most tyrosinase inhibitors.

These materials may be sold in the form of kits containing an effective amount of tyrosinase inhibitor in one container and an effective amount of interferon for anti-cancer therapy in another container for accurate sequential administration. The materials may also be prepared as a composition in which the effective amount of tyrosinase inhibitor is combined with the effective amount of interferon. Other known pharmaceutical excipients and carriers may also be present in such a composition as is entirely conventional.

No claim is being made herein that interferon, when administered in accordance with the process of the present invention, will be effective against every kind of cancer in humans. It is being claimed, however, that at least for any particular malignancy against which interferon is known to have some degree of effectiveness, this effectiveness will be increased by administration in accordance with the process of the present invention. Examples of malignancies against which clinical tests has been recorded with varying degrees of success are listed in the Sikora and Priestman reviews cited hereinabove which are hereby incorporated by reference.

The use of tyrosinase inhibitors without concommittant administration of interferon is also comprehended by the present invention, as natural interferon production of the patient can be expected to again become effective once the abnormally high tyrosinase activity has been eliminated. Accordingly, the administration of D-penicillamine in a manner discussed hereinabove may be used for the treatment of patients having malignancies with abnormally high tyrosinase activity without the simultaneous or subsequent administration of interferon.

While the use of specific tyrosinase inhibitors, i.e. certain dicarboxylic acids, has been suggested in the past for treatment of melanoma, (Nazzaro-Porro, M. et al "Identification of Tyrosinase Inhibitors in Cultures of Pityrosporum and their Melanocytotoxic Effect", *Pigment Cell*, vol. 4, pages 234–243 (Karger, Basel, 1979)), the use of noncompetitive inhibitors of tyrosinase has not been suggested for the treatment of neoplasms having abnormally high tyrosinase activity.

As discussed hereinabove, the optimum dose rate can be determined empirically, as is well known, without undue experimentation.

It will be obvious to those skilled in the art that various changes may be made without departing from the scope of the invention and the invention is not to be considered limited to what is described in the specification.

What is claimed is:

1. A method for improving the effectiveness of interferon in the treatment of neoplastic conditions accompanied by an increase of the patient's serum tyrosinase level substantially above normal, comprising administering an agent for inhibiting tyrosinase in an amount sufficient to substantially inactivate the tyrosinase in the serum of the patient being treated with interferon, and administering the interferon during the time in which the tyrosinase is being inhibited by said agent.

2. A method in accordance with claim 1, wherein said agent for inhibiting tyrosinase is selected from the group consisting of diethyldithiocarbamte, sodium sulfide, potassium ethyl xanthate, sodium azide, salicylaldoxime, p-aminobenzoic acid, sulfathiazole, thiouracils, thioureas, cysteine, D-penicillamine, glutathione, BAL (dimercaprol), and thioproline.

3. A method in accordance in claim 1, wherein said agent for inhibiting tyrosinase is D-penicillamine.

4. A method in accordance with claim 1, wherein said agent for inhibiting tyrosinase is a $C_{8-13}$ dicarboxylic acid.

5. A method in accordance with claim 1, wherein the agent for inhibiting tyrosinase is first administered and the interferon is subsequently administered during the time in which the tyrosinase is being inhibited by said agent.

6. A method in accordance with claim 1, wherein the agent for inhibiting tyrosinase and the interferon are administered simultaneously.

7. In a composition containing interferon and a pharmaceutically acceptable carrier or excipient, the improvement whereby the effectiveness of the interferon is increased, wherein the composition includes an amount of interferon effective for treatment of neoplastic conditions accompanied by an increase in the patient's serum tyrosinase level substantially above normal, and an agent for inhibiting tyrosinase in an amount effective to inactivate the tyrosinase in the serum of the patient.

8. A composition in accordance with claim 7, wherein said agent for inhibiting tyrosinase is selected from the group consisting of diethyldithiocarbamate, sodium sulfide, potassium ethyl xanthate, sodium azide, salicylaldoxime, p-aminobenzoic acid, sulfathiazole, thiouracils, thioureas, cysteine, D-penicillamine, glutathione, BAL (dimercaprol), and thioproline.

9. A composition in accordance with claim 7, wherein said agent for inhibiting tyrosinase is D-penicillamine.

* * * * *